United States Patent
Manke et al.

(10) Patent No.: US 9,119,919 B2
(45) Date of Patent: Sep. 1, 2015

(54) SYRINGE HAVING A SQUEEZE-FIT PLUNGER ROD

(71) Applicant: Becton Dickinson France, S.A.S., Le Pont-de-Claix (FR)

(72) Inventors: Darrin Scott Manke, North Andover, MA (US); Christopher Labak, Brookline, NH (US); Joseph Omer St. Cyr, Salem, NH (US)

(73) Assignee: Becton Dickinson France, S.A.S., Le Pont-de-Claix (FR)

( * ) Notice: Subject to any disclaimer, the term of this patent is extended or adjusted under 35 U.S.C. 154(b) by 349 days.

(21) Appl. No.: 13/622,390

(22) Filed: Sep. 19, 2012

(65) Prior Publication Data

US 2013/0085453 A1 Apr. 4, 2013

Related U.S. Application Data

(60) Provisional application No. 61/541,433, filed on Sep. 30, 2011.

(51) Int. Cl.
*A61M 5/315* (2006.01)
*A61M 5/50* (2006.01)
*A61M 5/31* (2006.01)

(52) U.S. Cl.
CPC ....... *A61M 5/31511* (2013.01); *A61M 5/31515* (2013.01); *A61M 5/5086* (2013.01); *A61M 2005/3104* (2013.01); *A61M 2005/3106* (2013.01); *A61M 2005/31518* (2013.01)

(58) Field of Classification Search
CPC .............. A61M 5/31511; A61M 5/31515; A61M 2005/31518; A61M 5/315
USPC .......... 604/187, 218, 219, 181, 228, 223, 221
See application file for complete search history.

(56) References Cited

U.S. PATENT DOCUMENTS

| | | | | |
|---|---|---|---|---|
| 3,115,135 A * | 12/1963 | Sarnoff | ......................... | 604/228 |
| 6,231,550 B1 | 5/2001 | Laughlin | | |
| 2003/0028151 A1* | 2/2003 | Righi et al. | ................... | 604/218 |
| 2011/0046569 A1* | 2/2011 | Lum et al. | ..................... | 604/219 |
| 2011/0046603 A1 | 2/2011 | Felsovalyi et al. | | |

FOREIGN PATENT DOCUMENTS

WO 2010/066588 A1 6/2010

* cited by examiner

*Primary Examiner* — Bhisma Mehta
*Assistant Examiner* — Nilay Shah
(74) *Attorney, Agent, or Firm* — The Webb Law Firm

(57) ABSTRACT

A syringe assembly having an exterior surface and defining a chamber having a stopper disposed therein is disclosed. The syringe assembly includes a plunger assembly having an elongated plunger rod and a handle portion connected thereto, the plunger rod including a depending leg and at least one hinge connecting the depending leg with the handle portion. The plunger rod is adapted to transition from a collapsed position, in which at least a portion of the depending leg extends along at least a portion of the exterior surface of a syringe barrel, to an extended position in which at least a portion of the depending leg engages the stopper. The at least one hinge maintains the depending leg substantially parallel to a longitudinal axis of the syringe barrel in both the collapsed position and the extended position.

20 Claims, 21 Drawing Sheets

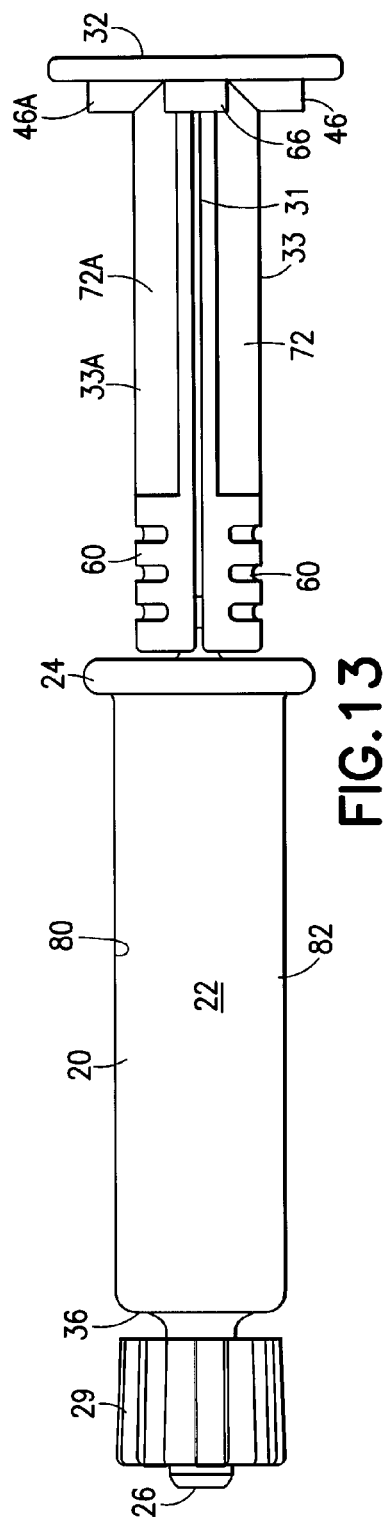
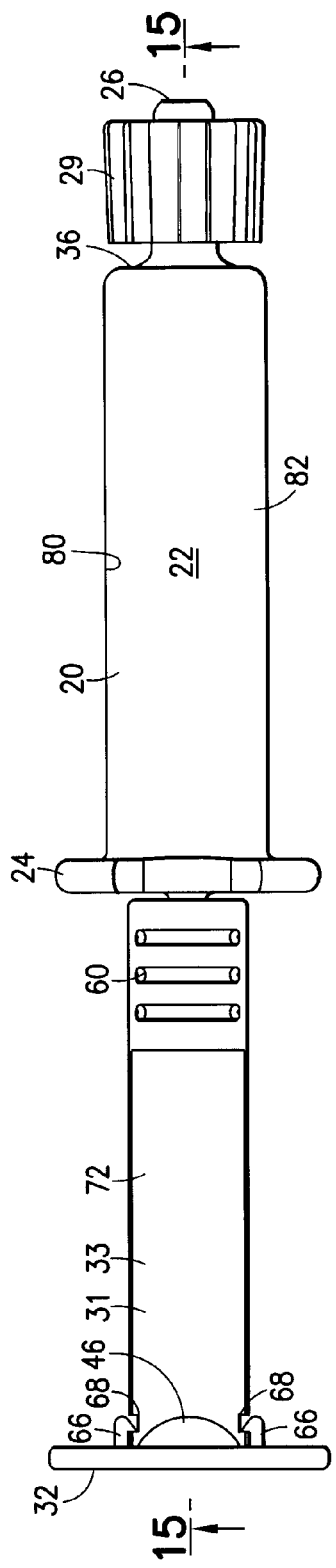
FIG.13
FIG.14

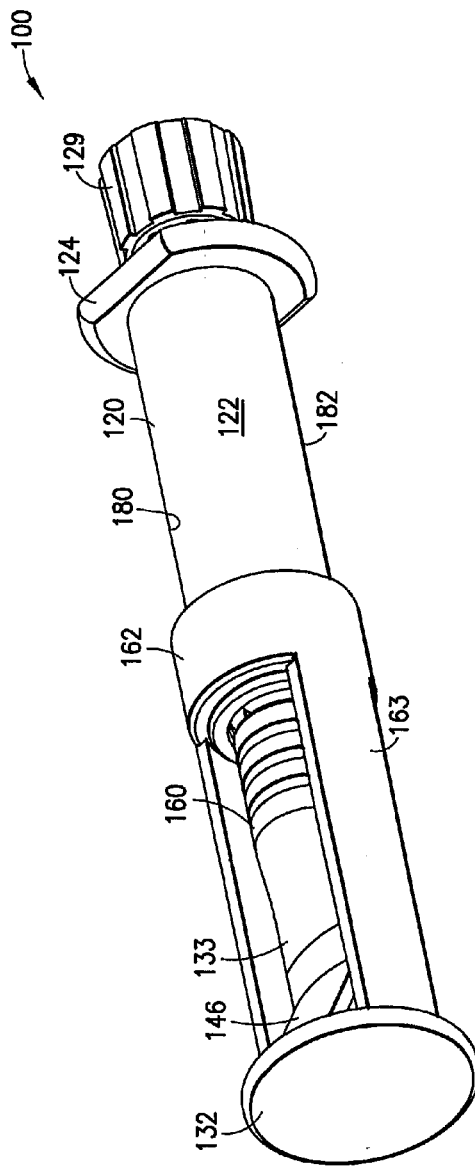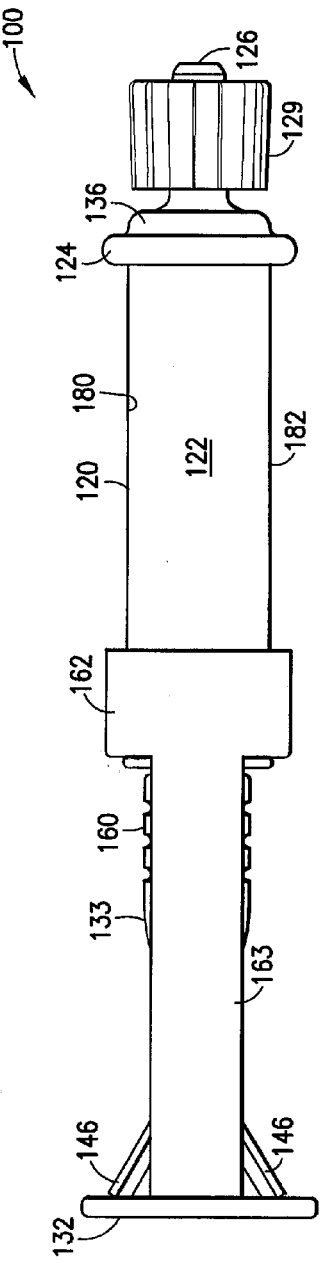
FIG. 25
FIG. 26

SYRINGE HAVING A SQUEEZE-FIT PLUNGER ROD

CROSS-REFERENCE TO RELATED APPLICATION

This application claims priority to U.S. Provisional Application Ser. No. 61/541,433 filed Sep. 30, 2011, the entire disclosure of which is hereby incorporated by reference.

BACKGROUND OF THE INVENTION

1. Field of the Invention

The present invention relates to a syringe assembly adapted for dispensing and delivery of a fluid. More particularly, the present invention is directed to a pre-filled syringe assembly having a transitionable plunger rod for reducing the overall dimension of the syringe assembly in the collapsed position.

2. Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger mechanism typically includes a plunger rod extending through the barrel, with a plunger head or stopper at the end of the plunger rod within the barrel, and with a finger flange at the other end of the plunger rod extending out of the barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depressing of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, wherein the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Packaging of such pre-filled syringes, however, tends to be bulky. A pre-filled syringe is typically packaged with the opening at the front end of the barrel including a separate cap thereover and with the plunger rod retracted out of the back end of the syringe barrel, with the fluid pre-filled within the syringe barrel. Such packaging creates an elongated package that can be awkward for shipping and storage.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint, to reduce the storage space required for containing the syringe. A smaller packaging footprint is also beneficial for end users who may carry the syringe with them in a pocket, purse or the like. It is also desirable to produce syringes that are uniform in terms of an outer surface shape to allow for stacking of these syringes within the storage cabinet.

Typical pre-filled hypodermic syringes have elongated plunger rods extending from beyond the proximal end of a syringe barrel to move the stopper through an injection cycle within the syringe barrel by linear actuation of the elongated plunger rod. This arrangement increases the length of the packaged syringe assembly, which increases costs associated with packaging the pre-filled syringe and takes up additional storage space.

SUMMARY OF THE INVENTION

Accordingly, there is a general need for a hypodermic syringe that has a reduced length and reduced packaging space when the syringe barrel is filled with a liquid medication prior to injection.

In accordance with an embodiment of the present invention, a syringe assembly includes a syringe barrel having a first end, a second end, and a sidewall extending therebetween having an exterior surface and an interior surface defining a chamber. The syringe assembly also includes a stopper disposed within the chamber of the syringe barrel and a plunger assembly. The plunger assembly includes an elongated plunger rod and a handle portion connected thereto, the plunger rod comprising a depending leg and at least one hinge connecting the depending leg with the handle portion. The plunger rod is adapted to transition from a collapsed position, in which at least a portion of the depending leg extends along at least a portion of the exterior surface of the syringe barrel, to an extended position in which at least a portion of the depending leg engages the stopper. At least one hinge maintains the leg portion substantially parallel to a longitudinal axis of the syringe barrel in both the collapsed position and the extended position.

In certain configurations, the syringe assembly includes a plurality of plunger rods connected to the handle assembly. Each of the plurality of plunger rods may include a depending leg and a hinge connecting the depending leg to the handle portion. In certain configurations, the plunger assembly may include a first plunger rod having a first depending leg connected to the handle portion by a first hinge, and a second plunger rod including a second depending leg connected to the handle portion by a second hinge. In this configuration, the first and second hinges maintain the first and second depending legs substantially parallel to each other in both the collapsed and the extended positions.

The stopper of the syringe assembly may also include an adapter having a plunger rod engagement for engaging at least a portion of the at least one depending leg in the extended position. The plunger rod may also include a distal end having an adapter engagement for engaging at least a portion of a stopper adapter coupled to the stopper in the extended position. Optionally, the stopper may include a stopper adapter having a protrusion, and the plunger rod may define a recess within a distal end thereof adapted to receive a portion of the protrusion therein in the extended position.

The syringe assembly may include a second plunger rod defining a second recess within the distal end thereof adapted to receive a portion of the protrusion therein in the extended position. The second plunger rod may be connected to the handle portion, and the second plunger rod may include a second depending leg and a second hinge connecting the second depending leg to the handle portion. The plunger rod and the second plunger rod may be isolated from each other in the collapsed position, and the plunger rod and the second plunger rod may engage each other in the extended position. The plunger rod may define a recess therein at a proximal end, and the second plunger rod may define a second recess therein at a proximal end, with the recess and second recess surrounding at least a portion of a stopper adapter coupled to the stopper in the extended position.

In certain configurations, the syringe assembly may include an outwardly extending flange disposed about a portion of the exterior surface of the sidewall of the syringe barrel. A portion of the plunger assembly may contact the outwardly extending flange in the collapsed position. The plunger rod may have a distal end and the plunger assembly may include a collar member extending from the handle. The syringe assembly may also include a second plunger rod including a second depending leg having a proximal end and a distal end, and a second hinge connecting the second depending leg to the handle portion at the proximal end, wherein the distal end of the second plunger rod is engaged with a portion of the stopper within the collar member in the extended position. The plunger rod and the second plunger rod may be oriented on substantially opposite sides of the collar member. The plunger rod and second plunger rod may deflect into the collar member in the extended position.

In another embodiment of the present invention, a syringe assembly includes a syringe barrel having a first end, a second end, and a sidewall extending therebetween having an exterior surface and an interior surface defining a chamber. The syringe assembly also includes a stopper including a stopper adapter having an engagement, with the stopper disposed within the chamber of the syringe barrel. The syringe assembly also includes a plunger assembly. The plunger assembly includes a handle portion, a first elongated plunger rod including a first depending leg and a first hinge connecting the first depending leg to the handle portion, and a second elongate plunger rod including a second depending leg and a second hinge connecting the second depending leg to the handle portion. The plunger assembly is adapted to transition from a collapsed position, in which at least a portion of the first depending leg and at least a portion of the second depending leg extend along at least a portion of the exterior surface of the syringe barrel, to an extended position in which at least a portion of the first depending leg and at least a portion of the second depending leg surround the engagement of the stopper.

In certain configurations, the first depending leg defines a first recess therein and the second depending leg defines a second recess therein. The engagement may be received within the first recess and the second recess in the extended position. The first plunger rod may have a distal end and the second plunger rod may have a distal end. The plunger assembly may also include a collar member engaged with the distal end of the first plunger rod and the distal end of the second plunger rod, with the collar member disposed about the exterior surface of the syringe barrel in the collapsed position.

In yet another embodiment of the present invention, a syringe assembly includes a syringe barrel having a first end, a second end, and a sidewall extending therebetween having an exterior surface and an interior surface defining a chamber. The syringe assembly also includes a stopper disposed within the chamber of the syringe barrel, and a plunger assembly. The plunger assembly includes an elongated plunger rod and a handle portion connected thereto. The plunger rod includes a depending leg and at least one hinge connecting the depending leg with the handle portion, with the depending leg having an inner surface substantially corresponding to the exterior surface of the syringe barrel. The plunger rod is adapted to transition from a collapsed position, in which at least a portion of the depending leg extends along at least a portion of the exterior surface of the syringe barrel, to an extended position in which at least a portion of the depending leg engages the stopper.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 13 is a left side view of the syringe assembly of FIG. 10 in accordance with an embodiment of the present invention.

FIG. 14 is a bottom view of the syringe assembly of FIG. 10 in accordance with an embodiment of the present invention.

FIG. 25 is a perspective view of the syringe assembly of FIG. 21 in an extended ready-to-use position in accordance with an embodiment of the present invention.

FIG. 26 is a right side view of the syringe assembly of FIG. 25 in accordance with an embodiment of the present invention.

DESCRIPTION OF PREFERRED EMBODIMENTS

Figure 1:
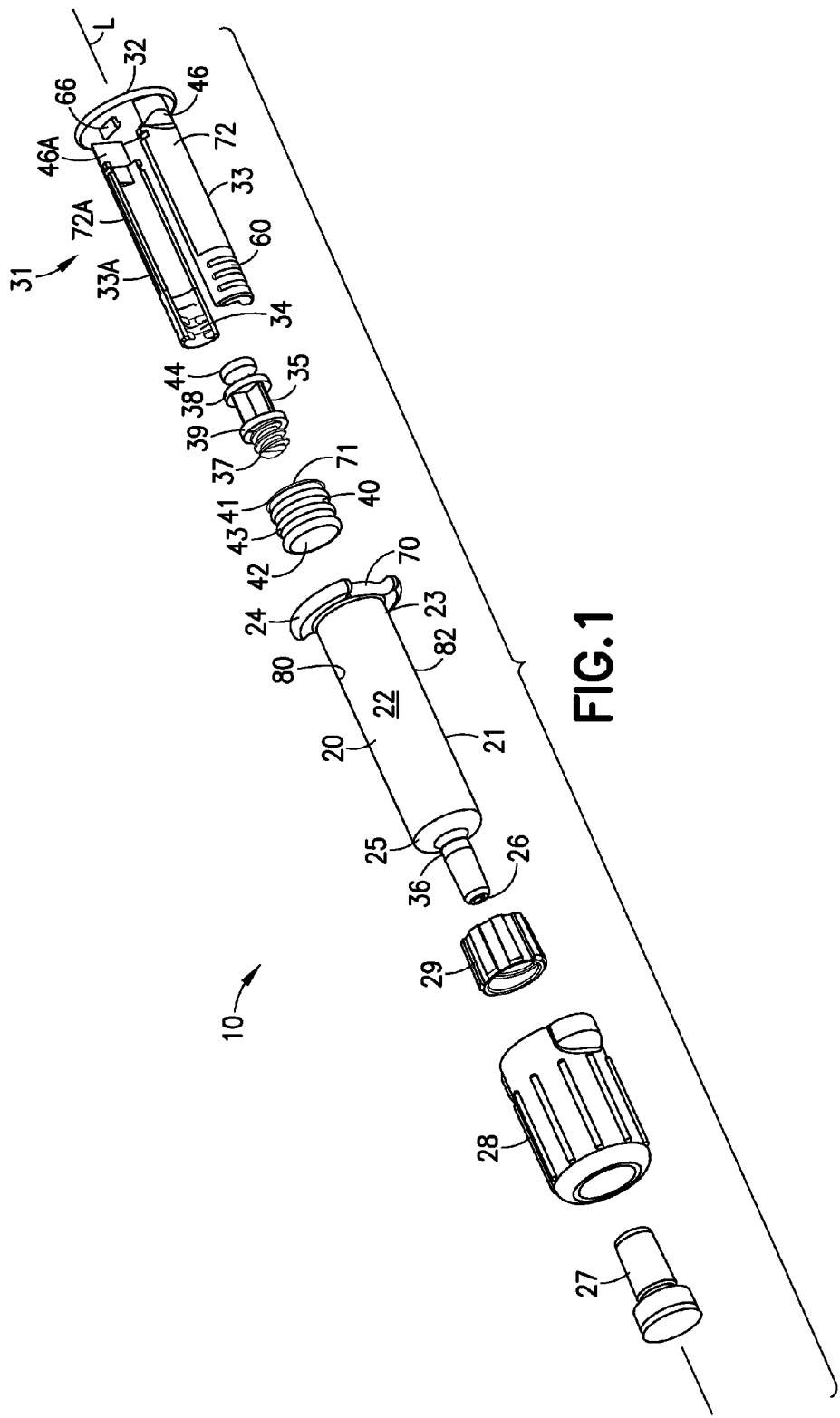
FIG. 1 is an exploded perspective view of a syringe assembly in accordance with an embodiment of the present invention.
Figure 2:
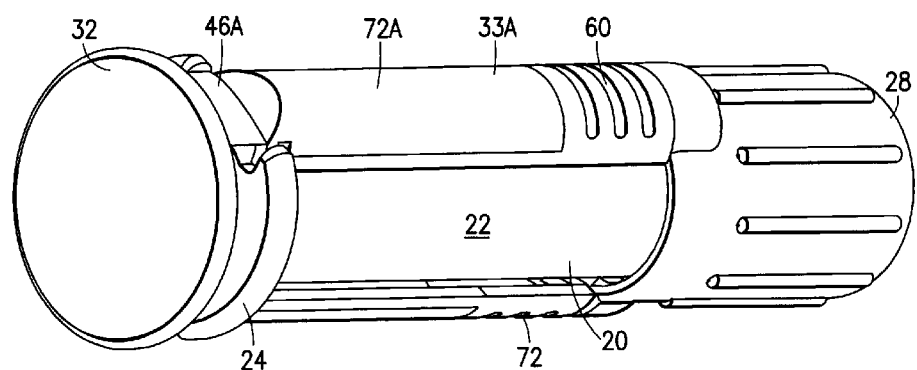
FIG. 2 is a perspective view of the syringe assembly of FIG. 1 in a first pre-use position in accordance with an embodiment of the present invention.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Referring to FIGS. 1-15, a syringe assembly, generally indicated as 10, adapted for the dispensing and delivery of a fluid is shown. Syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

The syringe assembly 10 includes a syringe barrel 20 having a first or distal end 25 and a second or proximal end 23, with a sidewall 21 extending therebetween and defining an interior chamber 22 of the syringe barrel 20. Syringe barrel 20 has an interior surface 80 and an exterior surface 82. The syringe barrel 20 may be in the general form of an elongated cylindrical barrel, as is known in the art for the general shape of a hypodermic syringe, although other forms for containing a fluid for delivery are also contemplated by the present invention. The syringe barrel 20 may be formed of glass, or may be injection molded from thermoplastic material such as polypropylene and polyethylene according to techniques known to those of ordinary skill in the art, though it is to be appreciated that the syringe barrel 20 may be made from other suitable materials and according to other applicable techniques. In certain configurations, the syringe barrel 20 may include an outwardly extending flange 24 about at least a portion of the proximal end 23. The flange 24 may be configured for easy grasping by a medical practitioner, as will be discussed herein.

The syringe barrel 20 may include markings, such as graduations on the sidewall 21 thereof, for providing an indication as to the level or amount of fluid contained within the syringe barrel 20. Such markings may be provided on the external wall, the internal wall, or integrally formed or otherwise within the wall of syringe barrel 20. Alternatively, or in addition thereto, the markings may provide a description of the contents of the syringe, or other identifying information, as may be known in the art.

The first or distal end 25 of syringe barrel 20 includes an outlet opening 26 which may have a profile adapted for engagement with a separate dispensing device, such as a needle assembly or IV connection assembly. In one embodiment, the first or distal end 25 may include a generally tapered luer connection 36 for engagement with an optional separate tapered luer structure (not shown), as is generally known. The outlet opening 26 of the syringe barrel 20 is provided in fluid communication with the chamber 22 and may be adapted to communicate with a needle cannula (not shown). A tip cap 29 including a plug 27 for sealing the outlet opening 26 may be provided over the outlet opening 26 in the initial pre-use position to maintain the sterility of the contents of the chamber 22. A secondary protective cover 28 may also be provided over the distal end 25 of the syringe barrel 20 providing a secondary cover for the outlet opening 26.

An outwardly extending flange 24 may also be provided about a portion of the sidewall 21 of the syringe barrel 20 to assist a medical practitioner in the handling of the syringe assembly 10. The outwardly extending flange 24 may extend radially outward from the exterior surface of the sidewall 21 of the syringe barrel 20 about a portion of the sidewall 21, such as about the proximal end 23. In one embodiment, the outwardly extending flange may include at least one recess 70 disposed within the flange 24. In another embodiment, the outwardly extending flange may include a plurality of recesses 70 disposed within the flange 24, such as a pair of recesses 70 disposed on substantially opposing sides of the outwardly extending flange 24 about the syringe barrel 20.

Referring again to FIGS. 1-15, a stopper 40 is slideably disposed within the chamber 22 of the syringe barrel 20. In an initial, pre-use position; as shown in FIGS. 2-9, the stopper 40 is positioned within the chamber 22 of the syringe barrel 20 at a position adjacent to the second or proximal end 23 of the syringe barrel 20. The stopper 40 includes a proximal surface 41, a distal surface 42, and a peripheral surface 43 extending between the proximal 41 and distal 42 surfaces. The peripheral surface 43 of the stopper 40 includes one or more sealing surfaces for sealingly engaging the interior of the sidewall 21 of the syringe barrel 20 so as to form a substantially fluid-impervious seal within the chamber 22.

An adapter 35 is coupled to stopper 40 via an engagement of a stopper engaging portion 37 of the adapter 35 and a corresponding adapter engaging portion 71 of the stopper 40. In one embodiment, the adapter 35 and the adapter engaging portion 71 each include corresponding threads for engagement therebetween. In a further embodiment, the stopper engaging portion 37 of the adapter 35 is provided adjacent a distal end 39 of the adapter, and the adapter engaging portion 71 of the stopper 40 is provided adjacent the proximal surface 41 of the stopper 40. In one embodiment, the adapter 35 and the stopper 40 are co-formed such that the stopper 40 includes the adapter 35. The adapter 35 includes a plunger rod engagement 44 extending from a proximal end 38 of the adapter 35.

The syringe assembly 10 also includes a plunger assembly 31. The plunger assembly 31 includes an elongated plunger rod 72 and a handle portion 32 connected thereto. In one embodiment, the plunger rod 72 extends substantially perpendicular to the handle portion 32. The plunger rod 72 includes a depending leg 33 and at least one hinge 46 connecting the depending leg 33 with the handle portion 32. In one embodiment, the depending leg 33 may be formed of a substantially rigid material and the hinge 46 may be formed of a substantially bendable material. In another embodiment, the depending leg 33 and the hinge 46 may be formed of the same material but have different treatment processes applied thereto to impart substantially rigid properties to the depending leg 33 and substantially flexible properties to the hinge 46. In a further embodiment, the hinge 46 may be a living hinge or a mechanical hinge affixed to the depending leg 33. In still a further configuration, the hinge 46 may connect the depending leg 33 to an intermediary member connected to a portion of the handle portion 32.

Figure 18:
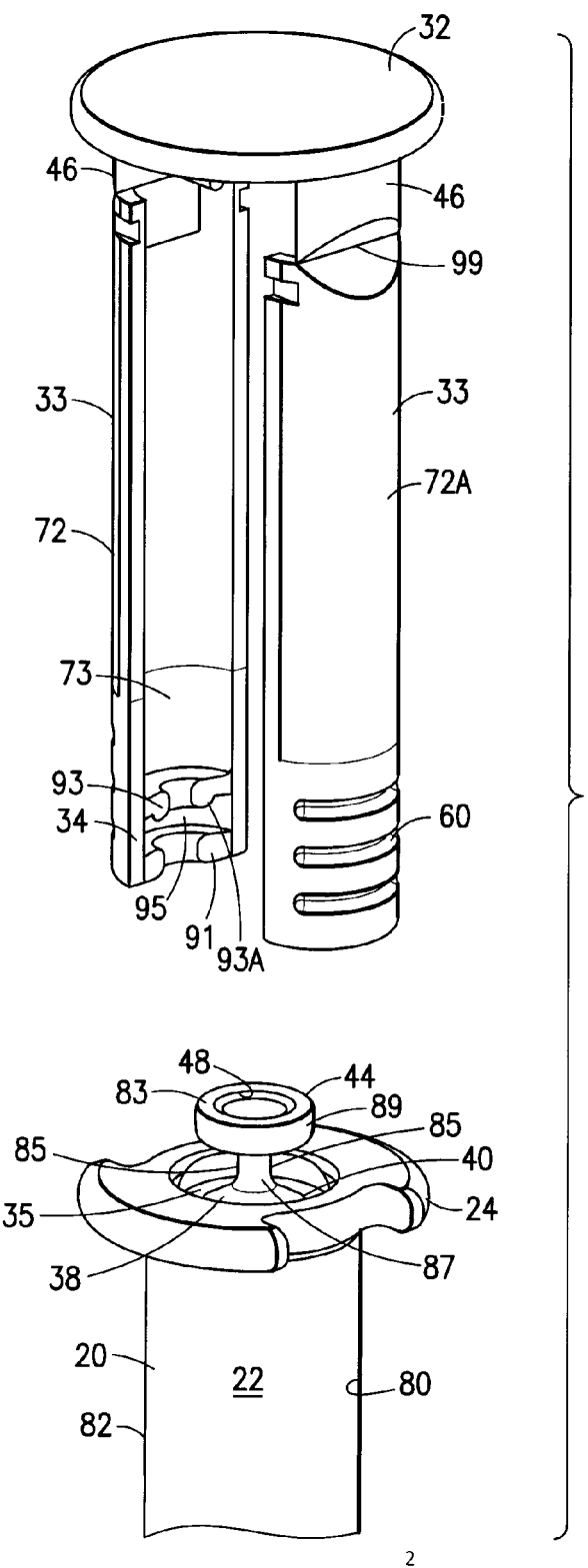
FIG. 18 is a partial perspective view of the plunger assembly and a plunger adapter of the syringe assembly of FIG. 16 in accordance with an embodiment of the present invention.

In a further configuration, as shown in FIG. 1, the plunger assembly 31 may include a plurality of elongate plunger rods 72, 72A connected to the handle portion 32. In this configuration, the plurality of elongated plunger rods 72, 72A may each include a depending leg 33 and a hinge 46 connecting the depending leg 33 to the handle portion 32. In one embodiment, the plunger assembly 31 includes the pair of elongated plunger rods 72, 72A disposed on substantially opposing sides of the handle portion 32. In another configuration, the pair of elongated plunger rods 72, 72A are disposed on opposing sides of a longitudinal axis L of the syringe assembly 10, as shown in FIG. 1. The elongated plunger rod 72 may include a distal end 60 having an interior surface 73, as shown in FIG. 18, including an adapter engagement 34, as will be described herein.

Figure 3:
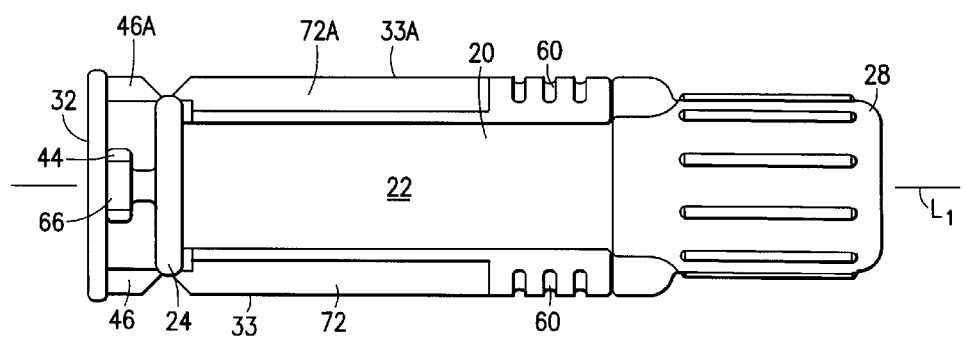
FIG. 3 is a right side view of the syringe assembly of FIG. 2 in accordance with an embodiment of the present invention.
Figure 4:
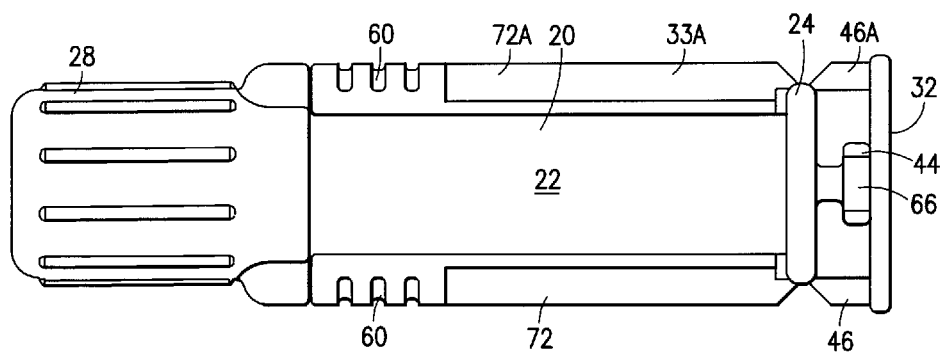
FIG. 4 is a left side view of the syringe assembly of FIG. 2 in accordance with an embodiment of the present invention.
Figure 5:
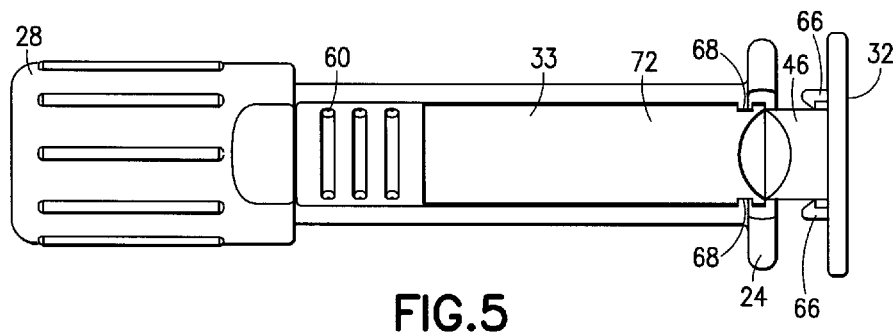
FIG. 5 is a top view of the syringe assembly of FIG. 2 in accordance with an embodiment of the present invention.
Figure 6:
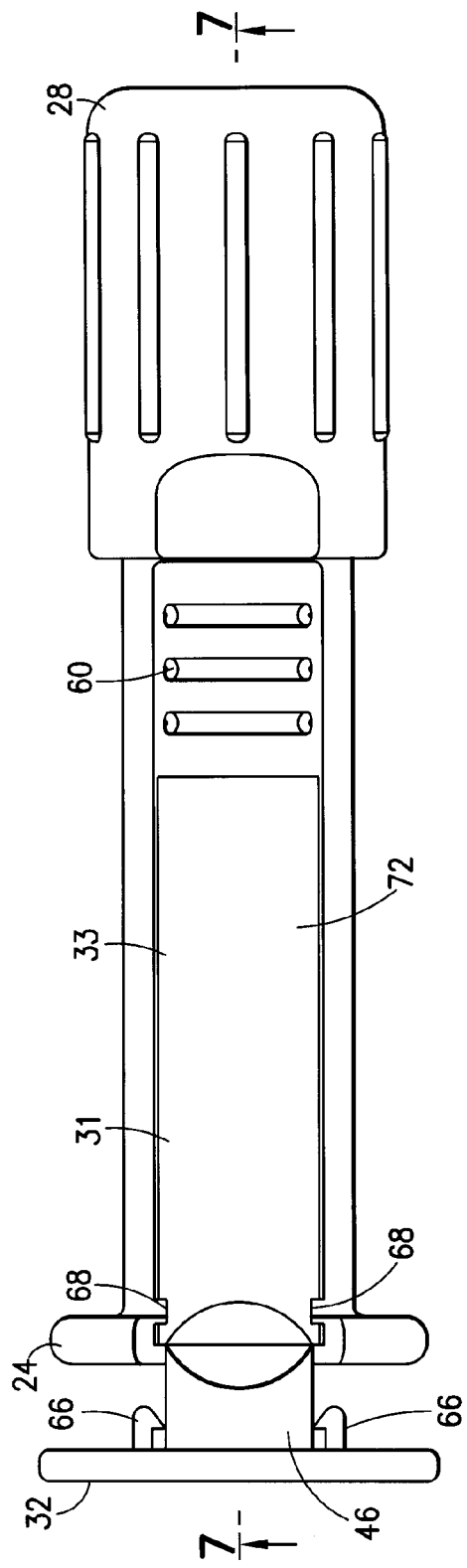
FIG. 6 is a bottom view of the syringe assembly of FIG. 2 in accordance with an embodiment of the present invention.
Figure 7:
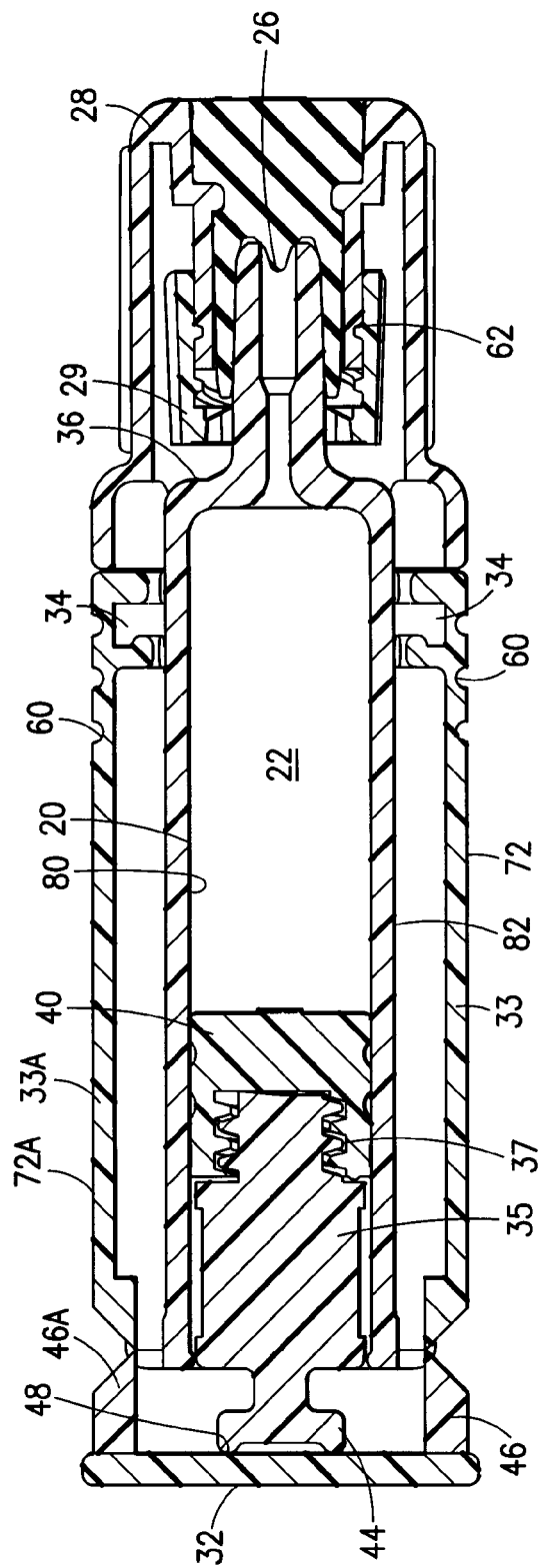
FIG. 7 is a cross-sectional view of the syringe assembly of FIG. 2 taken along line 7-7 of FIG. 6 in accordance with an embodiment of the present invention.
Figure 8:
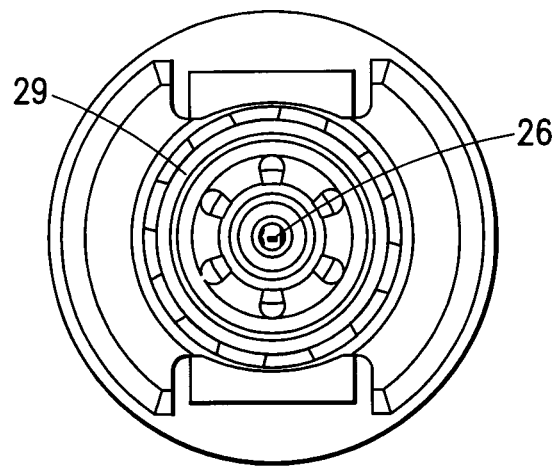
FIG. 8 is a front view of the syringe assembly of FIG. 1 having the cap removed therefrom in accordance with an embodiment of the present invention.
Figure 9:
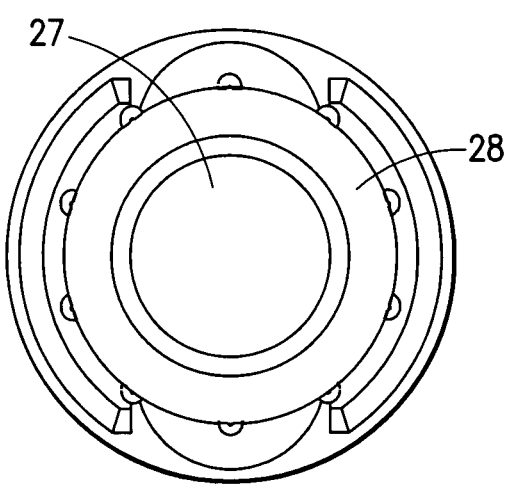
FIG. 9 is a front view of the syringe assembly of FIG. 2 in accordance with an embodiment of the present invention.
Figure 10:
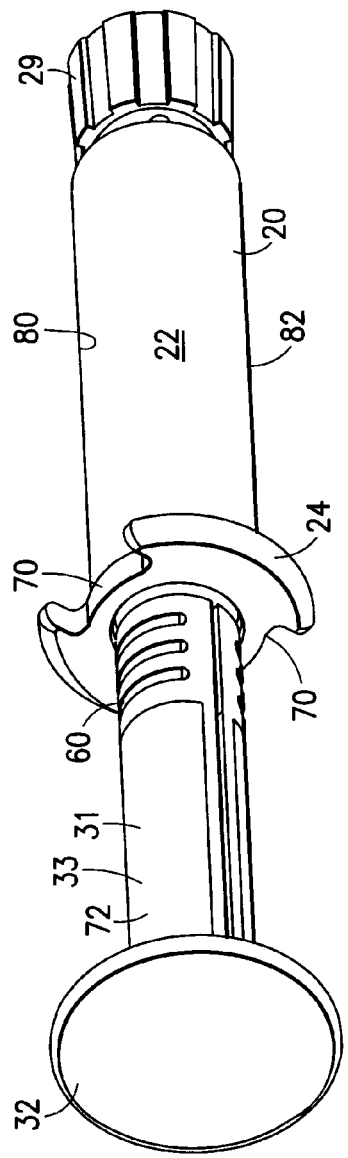
FIG. 10 is a perspective view of the syringe assembly of FIG. 1 in a second ready-to-use position in accordance with an embodiment of the present invention.

The plunger assembly 31 is adapted such that the elongated plunger rod 72 may transition from a first collapsed position, in which at least a portion of the depending leg 33 extends along at least a portion of the exterior surface 82 of the syringe barrel 20, as shown in FIGS. 2-9, to a second extended position in which at least a portion of the depending leg 33 engages the stopper 40 and/or stopper adapter 35, as shown in FIGS. 10-15. In the initial position, the plunger assembly 31 is disposed about the exterior surface 82 of the syringe barrel 20. In one configuration, the hinge 46 maintains the depending leg 33 substantially parallel to the longitudinal axis $L_1$ of the syringe barrel 20, as shown in FIG. 3, in the initial collapsed position. In a further configuration, the plunger assembly 31 includes a pair of elongated plunger rods 72, 72A, wherein each of hinges 46, 46A maintain a respective leg 33, 33A substantially parallel to the longitudinal axis $L_1$ of the syringe barrel 20, as shown in FIG. 3, in the initial collapsed position.

Figure 11:
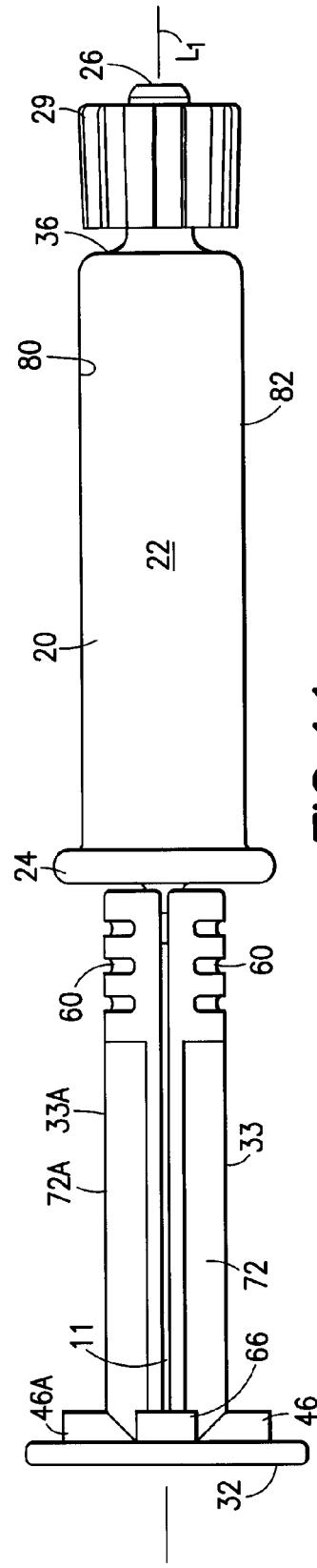
FIG. 11 is a right side view of the syringe assembly of FIG. 10 in accordance with an embodiment of the present invention.
Figure 12:
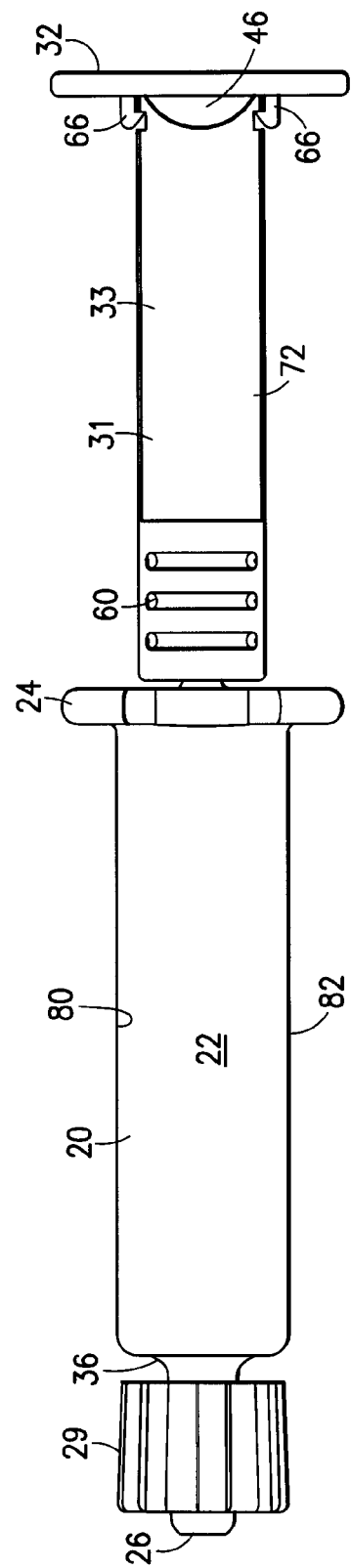
FIG. 12 is a top view of the syringe assembly of FIG. 10 in accordance with an embodiment of the present invention.
Figure 15:
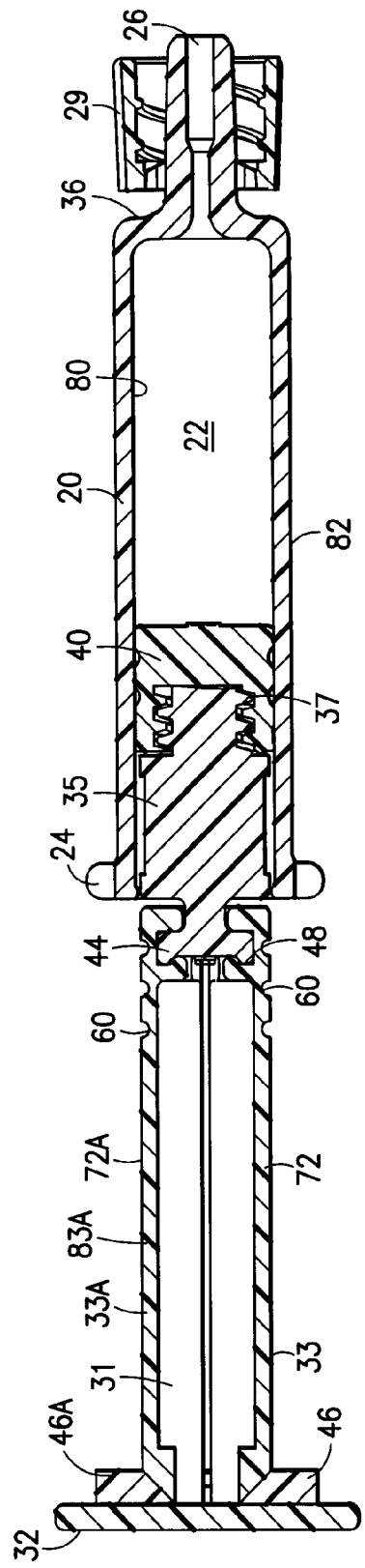
FIG. 15 is a cross-sectional view of the syringe assembly of FIG. 10 taken along line 15-15 of FIG. 14 in accordance with an embodiment of the present invention.

In the second, extended position, as shown in FIGS. 10-15, the plunger assembly 31 is configured such that the elongated plunger rod 72 engages a portion of the stopper 40 and/or the stopper adapter 35. In one configuration, as shown specifically in FIG. 11, the hinge 46 maintains the depending leg 33 substantially parallel to the longitudinal axis $L_1$ of the syringe barrel 20 in the extended position. In one configuration, a pair of elongated plunger rods 72, 72A engage a portion of the stopper 40 and/or the stopper adapter 35 in the elongated position. As specifically shown in FIG. 11, each hinge 46, 46A maintains the respective depending leg 33, 33A substantially parallel to the longitudinal axis $L_1$ of the syringe barrel 20 in the extended position. In a further configuration, each hinge 46, 46A maintains each respective leg 33, 33A substantially parallel to each other in both the collapsed position, as shown in FIG. 3, and the extended position, as shown in FIG. 11.

As shown specifically in FIG. 3, in the initial position, each of the plunger rods 72, 72A are isolated from each other in the collapsed position. As shown specifically in FIG. 11, each of the plunger rods 72, 72A engage each other in the extended position along a union surface 11 of the depending legs 33, 33A. Particular reference is now made to FIG. 6 in which locking tabs 66 may engage an indentation or cut-out 68 in the outwardly extending flange 24 in the collapsed position, shown in FIG. 6, to prevent premature disengagement of the plunger rod 72 from the collapsed position to the extended position.

Figure 16:
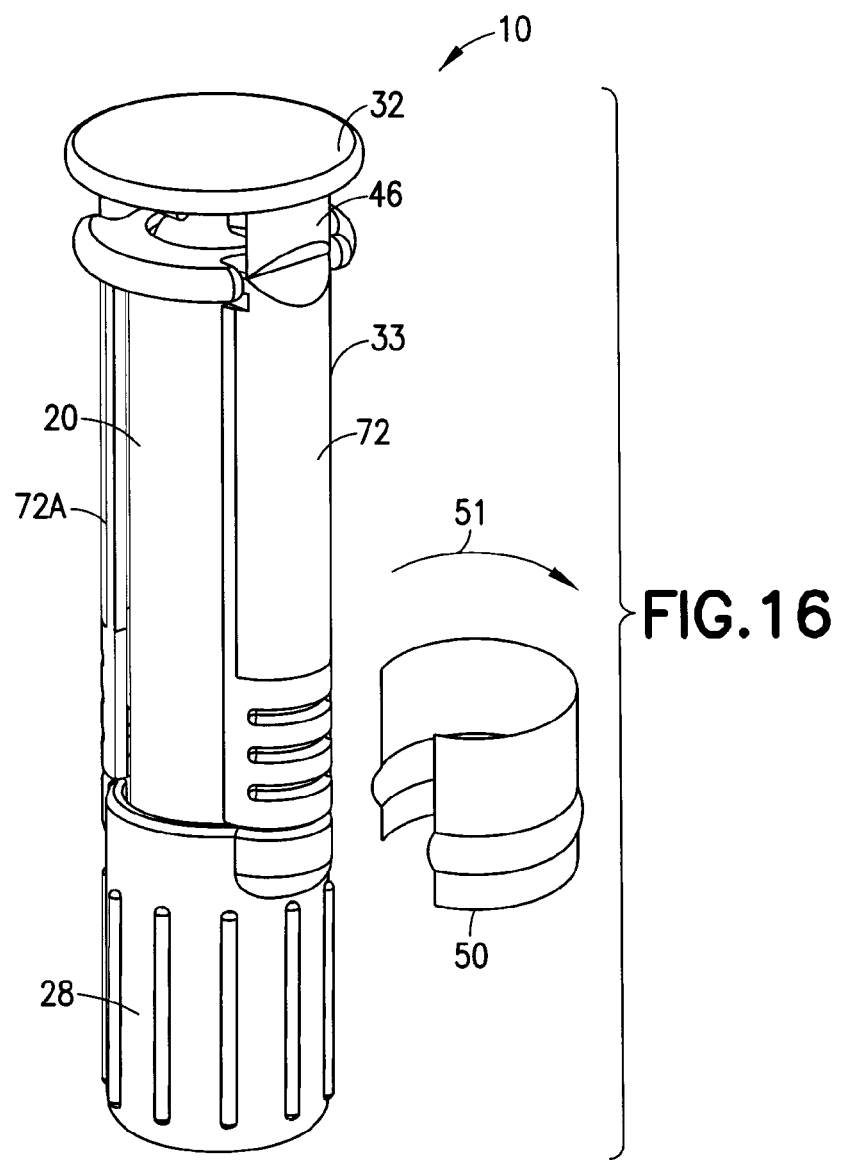
FIG. 16 is a perspective view of the syringe assembly of FIG. 1 in a pre-use position having a tamper evident band associated therewith in accordance with an embodiment of the present invention.
Figure 17:
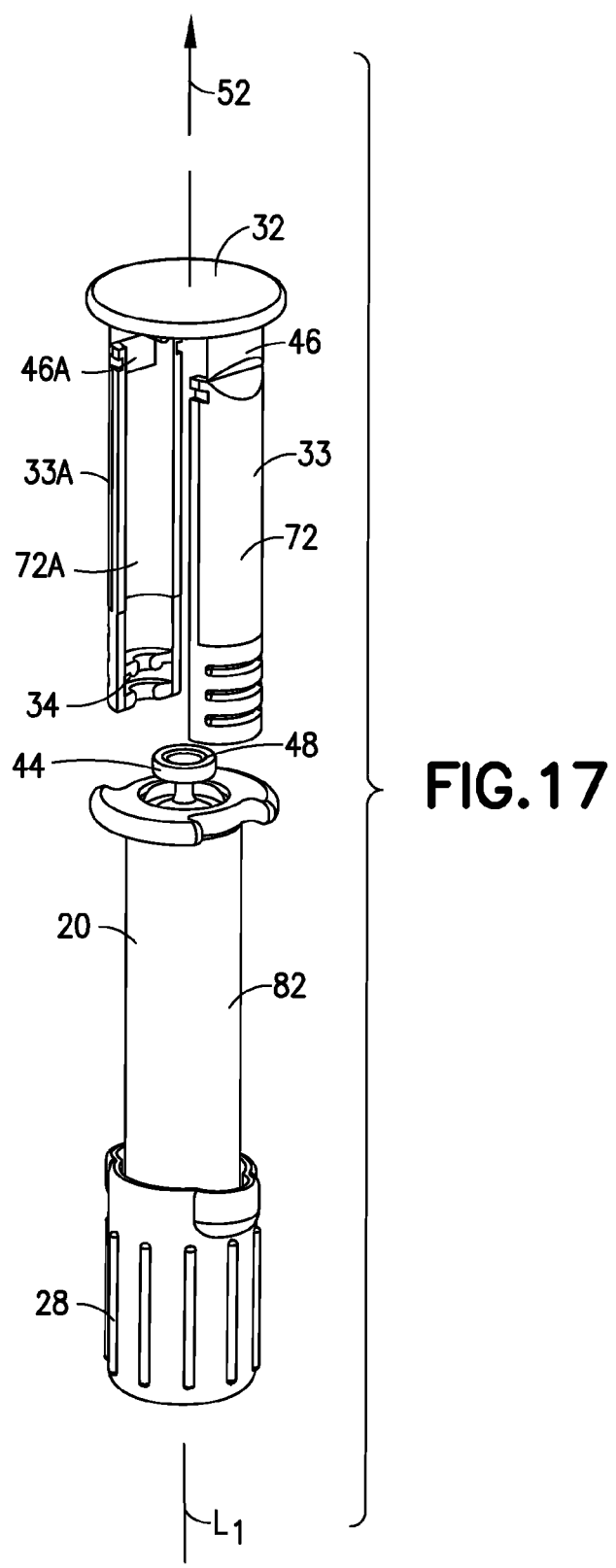
FIG. 17 is a perspective view of the syringe assembly of FIG. 16 having the plunger assembly removed therefrom in accordance with an embodiment of the present invention.

In use, a medical practitioner will transition the syringe assembly 10 from the initial collapsed position, as shown in FIG. 16, to an intermediate position, as shown in FIG. 17-18, in which the plunger assembly 31 is removed from engagement over at least a portion of the syringe barrel 20. In the initial position, the syringe assembly 10 may include a tamper evident band 50 disposed over a portion of the plunger assembly 31. The tamper evident band 50 may provide a further sealing mechanism to maintain the sterility of the interior of the syringe assembly 10, such as to maintain the sterility of the chamber 22 prior to use. The tamper evident band 50 may be formed of any material suitable to provide a sufficient seal over a portion of the plunger assembly 31 disposed over the syringe barrel 20. Tamper evident band 50 is formed of a breakable material that may not be reattached over the syringe assembly 10 once access to the interior of syringe assembly 10 has been initiated. A medical practitioner may remove the tamper evident band 50 by applying a force in the direction of arrow 51, as shown in FIG. 16.

Figure 19:
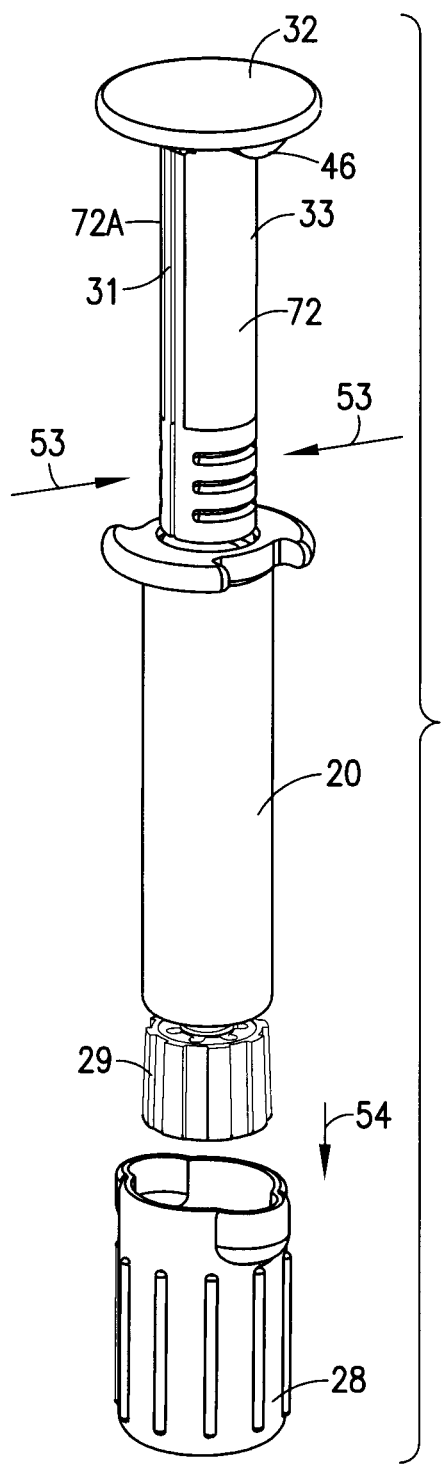
FIG. 19 is a perspective view of the syringe assembly of FIG. 16 having the plunger assembly engaged with a portion of the stopper in the ready-to-use position in accordance with an embodiment of the present invention.

Once the tamper evident band 50 has been removed from the syringe assembly 10, the medical practitioner may advance the plunger assembly in the proximal direction by applying a force to the handle portion 32 in the direction of arrow 52, as shown in FIG. 17. In one configuration, the plunger assembly 31 is loosely provided over the exterior surface 82 of the syringe barrel 20 and the hinge 46 applies no biasing force to the depending leg 33 in the compressed position. In order for a medical practitioner to initiate transition of the syringe assembly 10 from the collapsed position, as shown in FIG. 16, to the extended ready-to-use position, as shown in FIG. 19, the medical practitioner applies a compressive force to the plunger rod 72 in the direction of arrows 53, as shown in FIG. 19. In a further configuration, the medical practitioner may apply a compressive force to both plunger rods 72, 72A in the direction of arrows 53, as shown in FIG. 19.

In one configuration, the plunger rod 72 is advanced proximally over the exterior surface 82 of the syringe barrel 20 such that the hinge 46 biases the depending leg 33 against the exterior surface 82 of the syringe barrel 20 to maintain the plunger rod 72 in an orientation substantially parallel to the longitudinal axis $L_1$ of the syringe barrel 20. In another configuration, both plunger rods 72, 72A are advanced proximally over the exterior surface 82 of the syringe barrel 20 such that both hinges 46, 46A bias the corresponding depending legs 33, 33A against the exterior surface 82 of the syringe barrel 20 to maintain the plunger rods 72, 72A in an orientation substantially parallel to the longitudinal axis $L_1$ of the syringe barrel 20. Transition of the syringe assembly 10 from the collapsed position, shown in FIG. 16, to the extended position in which a portion of the plunger rod 72 engages a portion of the stopper 40 and/or adapter 35, shown in FIG. 19, occurs automatically in this configuration. Hinges 46, 46A immediately transition the plunger rods 72, 72A to encompass a portion of the stopper 40 and/or adapter 35 once the bias of the depending leg 33, 33A against the syringe barrel 20 is removed by the proximal advancement of the plunger rods 72, 72A, in the direction of arrow 52 of FIG. 17, out of engagement with the syringe barrel 20. In one configuration, hinges 46 may be adapted to hinge inwardly along a hinge line 99, shown in FIG. 18, thereby transitioning the plunger rod 72 from a position along the exterior surface 82 of the syringe barrel 20 to a position wherein the plunger rod 72 may be advanced within the chamber 22 of the syringe barrel 20. In still a further embodiment, the plunger rods 72, 72A may be withdrawn over the syringe barrel 20 in the proximal direction through recesses 70 defined within the outwardly extending flange 24.

With specific reference to FIG. 18, the stopper 40 and/or stopper adapter 35 may include a plunger rod engagement 44, such as a protrusion 89, extending from a proximal surface 38 of the stopper adapter. Protrusion 89 may include an annular recess 48 disposed within a top surface 83. Protrusion 89 may also define a notch portion 85 extending about a neck portion 87, and may be disposed between the proximal surface 41 of the stopper 40 and/or stopper adapter 35 and the plunger rod engagement 44.

The plunger rod 72 may also include an adapter engagement 34. In one configuration, the adapter engagement 34 is disposed adjacent the distal end 60 of the plunger rod 72. In a further configuration, the adapter engagement 34 is disposed on an interior surface 73 of the distal end 60. In still a further configuration, the adapter engagement 34 includes a first protruding band 91 engaged with the plunger rod 72 at a first location and a second protruding band 93 engaged with the plunger rod 72 at a second location with a recess 95 defined therebetween. In a further embodiment, a pair of plunger rods 72, 72A each include identical corresponding first protruding bands 91, second protruding bands 93, and recesses 95 defined therebetween.

In the extended position, as shown in FIG. 19, the adapter engagement 34, as shown in FIG. 18, of the plunger rod 72 engages at least a portion of the stopper adapter 35 and/or stopper 40. In one configuration, the recess 95 of the plunger rod 72 is adapted to receive a portion of the protrusion 89 therein, such that the first protruding band 91 is engaged within the notch portion 85 and the second protruding band 93 contacts the annular recess 48 of the protrusion 89. In one configuration, the second protruding band 93 may have an extension 93A for extending at least partially into the annular recess 48 in the extended position.

In a further configuration, a first plunger rod 72 and a second plunger rod 72A, each having corresponding first protruding bands 91, second protruding bands 93, and recesses 95 defined therebetween, receive a portion of the protrusion 89 in the recesses 95. In a further configuration, the recess 95 of the first plunger rod 72 and the recess of the second plunger rod 72A form a substantially circular restraint around the protrusion 89. In still a further configuration, in the extended position, at least a portion of the depending leg 33 of the plunger rod 72 and a portion of the depending leg 33A of the plunger rod 72A surround the plunger rod engagement 44, such as protrusion 89, of the stopper 40 and/or adapter 35.

Figure 20:
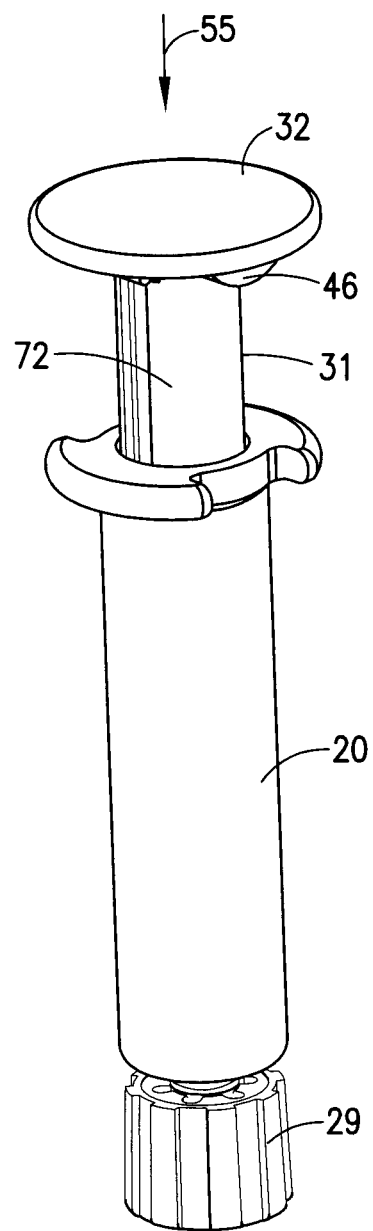
FIG. 20 is a perspective view of the syringe assembly of FIG. 16 in the used position in accordance with an embodiment of the present invention.
Figure 21:
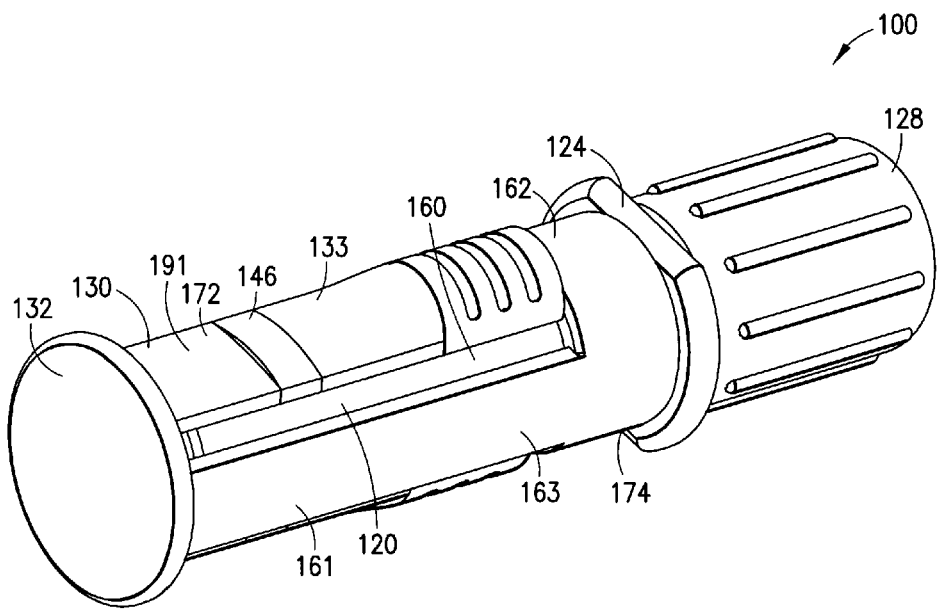
FIG. 21 is a perspective view of the syringe assembly in a first pre-use position in accordance with an embodiment of the present invention.

Once the plunger rod 72 and/or pair of plunger rods 72, 72A are engaged with a portion of the stopper 40 and/or adapter 35, such as the protrusion 89, the syringe assembly 10 is in the extended position. The protective cover 28 may be removed from covering the outlet opening 26 of the syringe barrel 20 in the direction of arrow 54, as shown in FIG. 19. The plunger rod 72 may then be moved axially as indicated by arrow 55, as shown in FIG. 20, to advance the plunger rod 72 to move the stopper 40 within the chamber 22 of the syringe barrel 20 to expel the contents therefrom in a conventional form. In one embodiment, a medication or drug may be disposed within the chamber 22 of the syringe barrel 20, and the advancement of the plunger rod 72 may expel the medication or drug from the syringe assembly 10.

It is to be appreciated that the syringe assembly 10 according to the present embodiment is particularly suitable for use as a pre-filled syringe with the stopper 40 provided at the second or proximal end 23 of the syringe barrel 20. Alternatively, the plunger assembly 31 could be used to pull the stopper 40 proximally so as to aspirate an empty syringe barrel 20. Syringe assembly 10 may be further provided with a mechanism so as to prevent re-use of the device. For example, the engagement between plunger rod 72 and the stopper 40 may be provided by an engagement between depending legs 33 and adapter 35. This engagement may be a one-way engagement, in that once depending legs 33 are locked onto the adapter 35, any attempt to retract the plunger rod 72 will cause the attachment between depending legs 33 and adapter 35 to detach or otherwise break or shear, thereby preventing re-use of the device.

It is also to be appreciated that the syringe assembly 10 according to the present embodiment allows for the overall length of a pre-filled syringe to be minimized for packaging and storage savings and to reduce storage space in medicine drawers.

With reference to FIGS. 21-29, a syringe assembly 100 according to a further embodiment of the present invention is shown. The syringe assembly 100 operates in a manner similar to the syringe assembly 10 discussed above with reference to FIGS. 1-20.

Referring to FIGS. 21-29, a syringe assembly, generally indicated as 100, includes a syringe barrel 120, with a sidewall 121 extending therebetween having an interior surface 180 and defining an interior chamber 122 of the syringe barrel 120. Syringe barrel 120 may include an outwardly extending flange 124, as discussed above. The syringe barrel 120 may also include an outlet opening 126 and may include a generally tapered luer connection 136. The syringe assembly 100 may also include a protective cover 128 disposed over the outlet opening 126. The syringe assembly 100 also includes a stopper 140 disposed within the chamber 122 of the syringe barrel 120 and including an adapter 135 having a plunger rod engagement 144, as described above.

Figure 22:
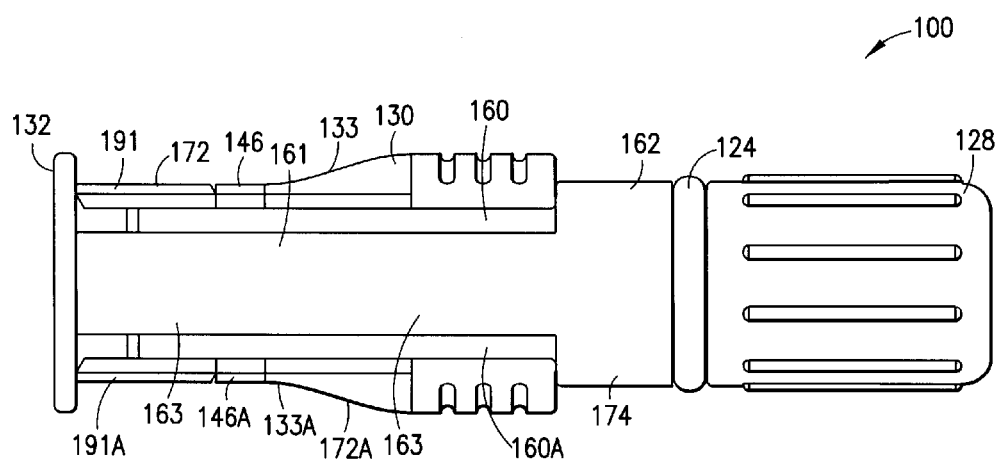
FIG. 22 is a right side view of the syringe assembly of FIG. 21 in accordance with an embodiment of the present invention.
Figure 23:
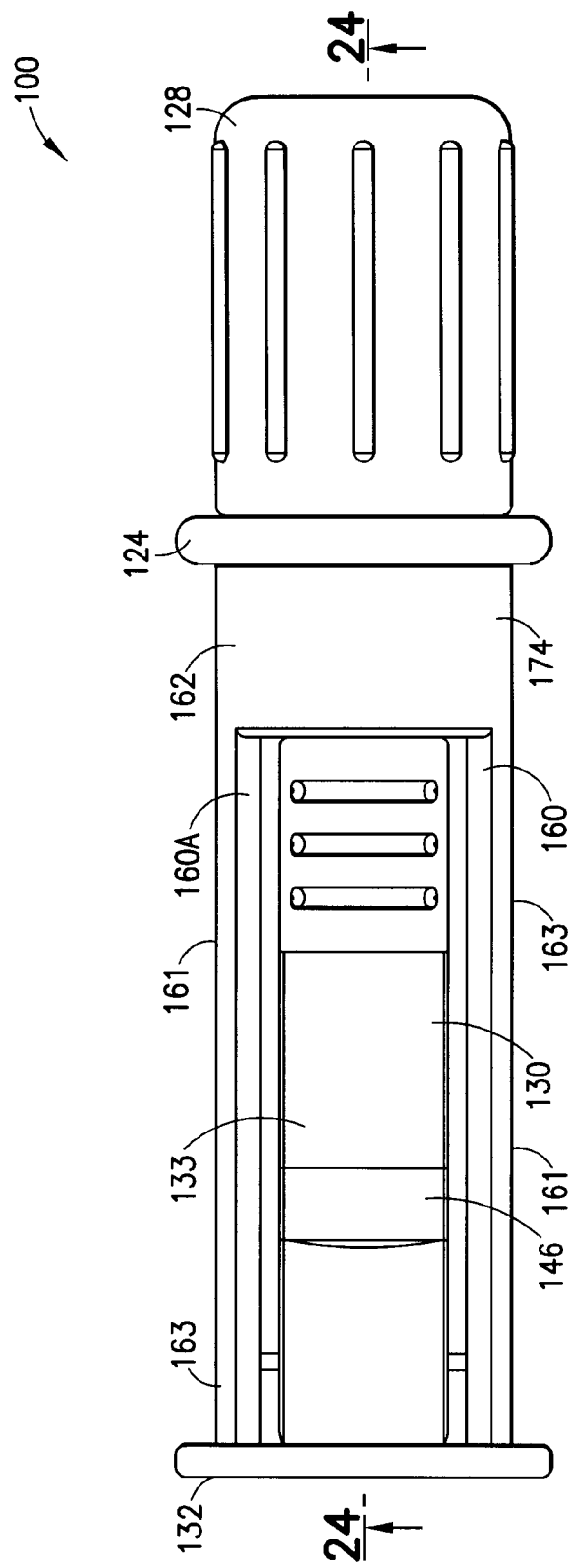
FIG. 23 is a bottom view of the syringe assembly of FIG. 21 in accordance with an embodiment of the present invention.

With further reference to FIGS. 21-29, the syringe assembly 100 also includes a plunger assembly 130. The plunger assembly 130 includes a handle portion 132 an elongated plunger rod 172 depending therefrom, and an adapter engagement 134 is disposed adjacent the distal end 160 of the plunger rod 172, as similarly described above with reference to FIGS. 1-20. The plunger rod 172 includes a depending leg 133 connected to the handle portion 132 by a hinge 146. In one embodiment, the hinge 146 connects the depending leg 133 to the handle portion 132 through connection to an intermediary portion 191. In a further embodiment, the plunger assembly 130 includes a second plunger rod 172A, as shown in FIG. 22, including a depending leg 133A connected to the handle portion 132 by a hinge 146A. In a further configuration, the hinge 146A connects the depending leg 133A to the handle portion 132 through connection to an intermediary portion 191A. In a further configuration, the plunger rod 172 and the second plunger rod 172A are engaged with the handle portion 132 on substantially opposing sides of the plunger assembly 130, as shown in FIG. 22.

The plunger assembly 130 may also include a collar member 163 depending from the handle portion 132. In one configuration, the collar member 163 includes an arm portion 161 extending substantially parallel to the plunger rod 172 and/or the second plunger rod 172A in the collapsed position, as shown in FIGS. 21-24. In a further configuration, the collar member 163 includes a plurality of arm portions 161 extending substantially parallel to the plunger rod 172 and/or second plunger rod 172A in the collapsed position. In the initial collapsed position, the arm portion 161 may be disposed over an exterior surface of the syringe barrel 120. The collar member 163 may also include a collar member band 162 connected to the arm portion 161 and circumferentially disposed about the exterior surface of the syringe barrel 120. In one embodiment, the collar member band 162 may be continuous about the syringe barrel 120. In another embodiment, the collar member band 162 extends about a portion of the exterior surface of the syringe barrel 120. In a further embodiment, the plurality of arm portions 161 and the collar member band 162 define a first window 160 adjacent the plunger rod 172, and a second window 160A adjacent the second plunger rod 172A.

Figure 24:
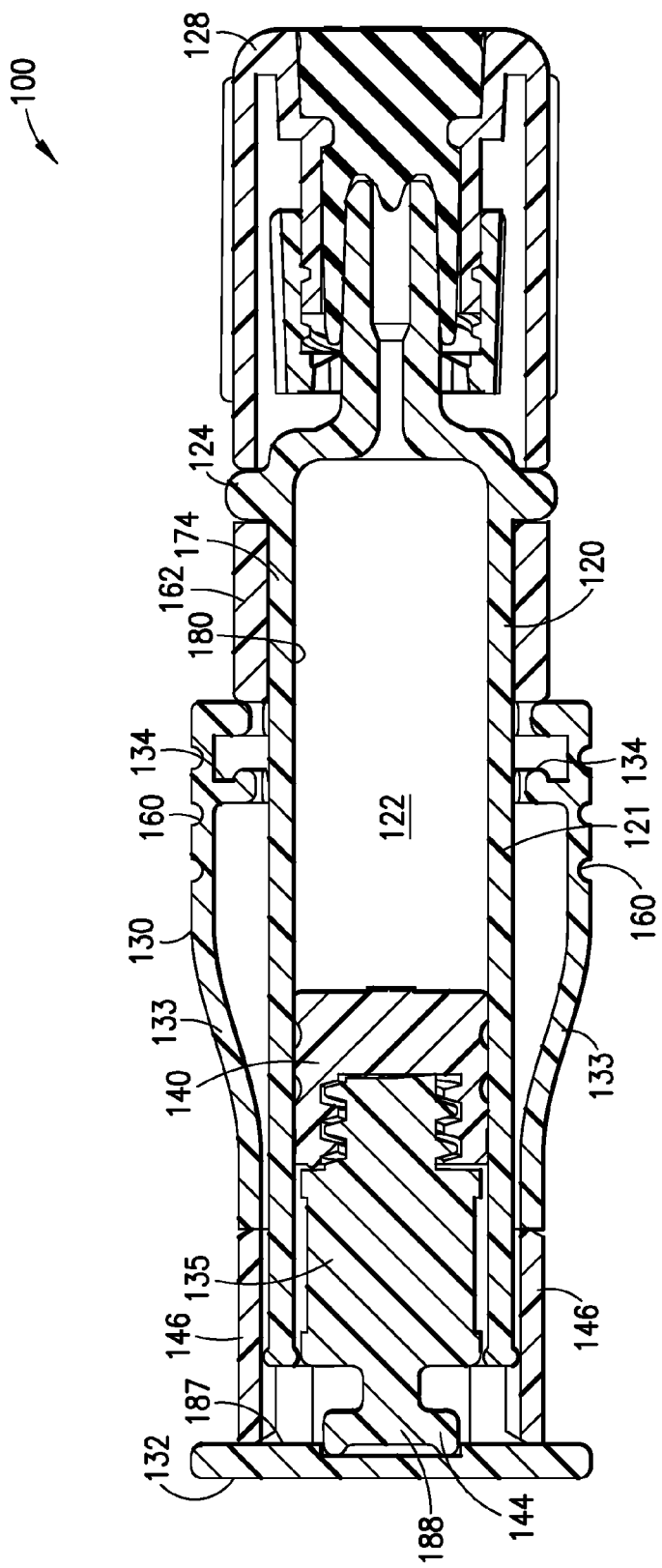
FIG. 24 is a cross-sectional view of the syringe assembly of FIG. 21 taken along line 24-24 of FIG. 23 in accordance with an embodiment of the present invention.
Figure 27:
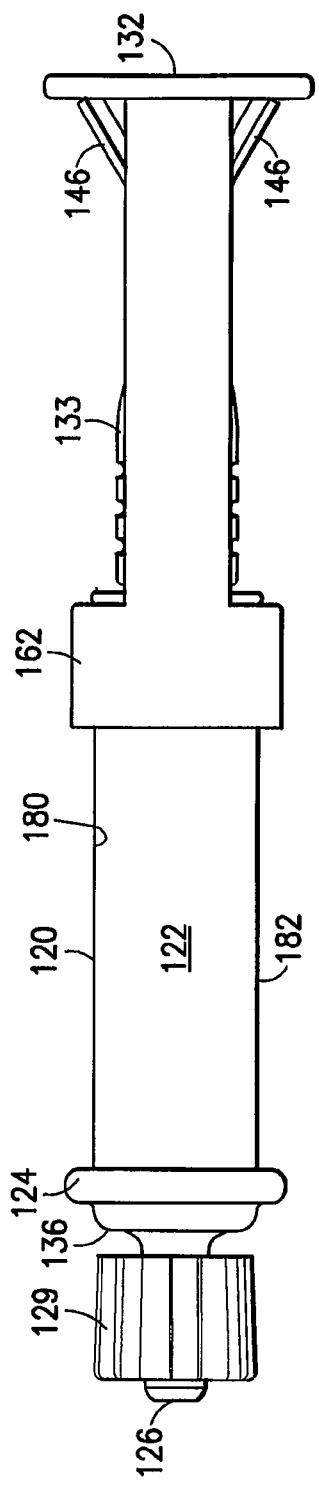
FIG. 27 is a left side view of the syringe assembly of FIG. 25 in accordance with an embodiment of the present invention.
Figure 28:
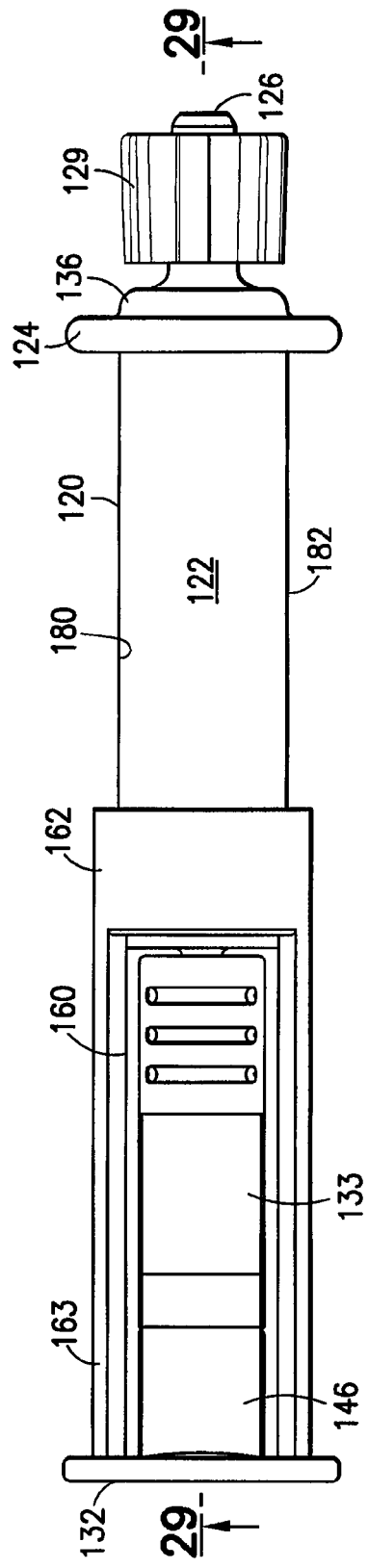
FIG. 28 is a bottom view of the syringe assembly of FIG. 25 in accordance with an embodiment of the present invention.
Figure 29:
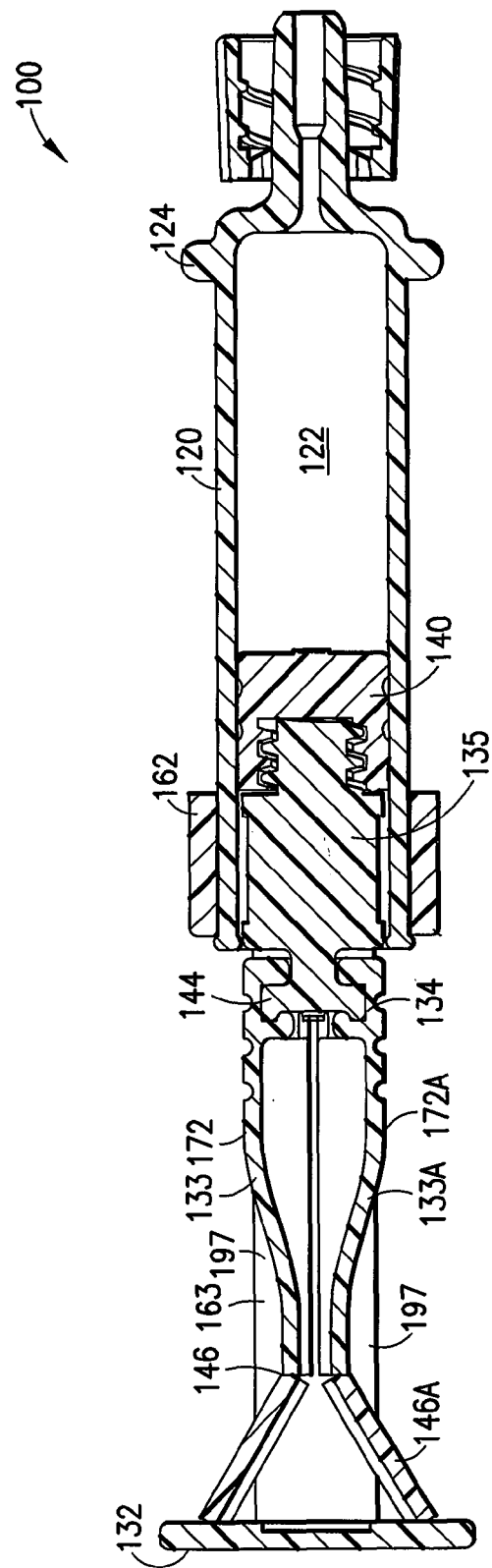
FIG. 29 is a cross-sectional view of the syringe assembly of FIG. 25 taken along line 29-29 of FIG. 28 in accordance with an embodiment of the present invention.

Referring specifically to FIGS. 21-24, the plunger assembly 130 in the collapsed position may be oriented such that the plunger rod 172 extends outwardly from first window 160, and the second plunger rod 172A extends outwardly from the second window 160A. In this configuration, the collar member band 162 is disposed about an external surface of the syringe barrel 120 adjacent a distal end 174 of the syringe barrel 120. In a further configuration, an interior surface 187, as shown in FIG. 24, of the handle portion 132 and a proximal end 188 of the adapter 135 may include a detent arrangement for securing the plunger assembly 130 with the adapter 135 in the collapsed position to prevent inadvertent transition to the extended position, as shown in FIGS. 25-29.

In this configuration, when the plunger assembly 130 is transitioned from the collapsed position, as shown in FIGS. 21-24, to the extended position, as shown in FIGS. 25-29, the hinges 146, 146A deflect into an interior 197 of the collar member 163 thereby causing the depending legs 133, 133A of the plunger rods 172, 172A to transition from a position along the exterior surface 182 of the syringe barrel 120 to a position in which at least a portion of the plunger rods 172, 172A engage the stopper 140 and/or adapter 135. In this configuration, the plunger rod 172 and the second plunger rod 172A deflect into the interior 197 of the collar member 163 in the extended position. In the extended position, the collar member 163 is adapted to be disposed over an exterior surface of the syringe barrel 120, and the plunger rod 172 and second plunger rod 172A are adapted to be at least partially disposed within the chamber 122. The plunger rod 172 and second plunger rod 172A also include an engagement with a portion of the stopper 140 and/or adapter 135, as discussed above with reference to FIGS. 1-20.

It is also to be appreciated that the syringe assembly 100 according to the present embodiment allows for the overall length and width of a pre-filled syringe to be minimized for packaging and storage savings and to reduce storage space in medicine drawers.

While several embodiments of a syringe assembly that have a transitionable plunger rod were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

The invention claimed is:

1. A syringe assembly, comprising:
   a syringe barrel having a first end, a second end, and a sidewall extending therebetween having an exterior surface and an interior surface defining a chamber;
   a stopper disposed within the chamber of the syringe barrel; and
   a plunger assembly comprising an elongated plunger rod and a handle portion connected thereto, the plunger rod comprising a depending leg and at least one hinge connecting the depending leg with the handle portion,
   wherein the plunger rod is adapted to transition from a collapsed position, in which the entirety of the plunger rod is external to the syringe barrel and at least a portion of the depending leg extends along at least a portion of the exterior surface of the syringe barrel, to an extended position in which at least a portion of the depending leg engages the stopper, and
   wherein the at least one hinge maintains the depending leg substantially parallel to a longitudinal axis of the syringe barrel in both the collapsed position and the extended position.

2. The syringe assembly of claim 1, further comprising a plurality of plunger rods connected to the handle portion.

3. The syringe assembly of claim 2, wherein the plurality of plunger rods each comprise a depending leg and a hinge connecting the depending leg to the handle portion.

4. The syringe assembly, of claim 2, wherein the plunger assembly comprises a first plunger rod comprising a first depending leg connected to the handle portion by a first hinge, and a second plunger rod comprising a second depending leg connected to the handle portion by a second hinge, wherein the first and second hinges maintain the first and second depending legs substantially parallel to each other in both the collapsed and the extended positions.

5. The syringe assembly of claim 1, wherein the stopper comprises an adapter having a plunger rod engagement for engaging at least a part of the depending leg in the extended position.

6. The syringe assembly of claim 1, wherein the plunger rod includes a distal end having an adapter engagement for engaging at least a portion of a stopper adapter coupled to the stopper in the extended position.

7. The syringe assembly of claim 1, wherein the stopper comprises a stopper adapter having a protrusion, and the plunger rod defines a recess within a distal end thereof adapted to receive a portion of the protrusion therein in the extended position.

8. The syringe assembly of claim 7, further comprising a second plunger rod defining a second recess within a distal end thereof adapted to receive a portion of the protrusion therein in the extended position.

9. The syringe assembly of claim 1, further comprising a second plunger rod connected to the handle portion, the second plunger rod comprising a second depending leg and a second hinge connecting the second depending leg to the handle portion, wherein the plunger rod and the second plunger rod are isolated from each other in the collapsed position, and the plunger rod and the second plunger rod engage each other in the extended position.

10. The syringe assembly of claim 9, wherein the plunger rod defines a recess therein at a proximal end, and the second plunger rod defines a recess therein at a proximal end, the recess defined by the plunger rod and the recess defined by the second plunger rod surrounding at least a portion of a stopper adapter coupled to the stopper in the extended position.

11. The syringe assembly of claim 1, further comprising an outwardly extending flange disposed about a portion of the exterior surface of the sidewall of the syringe barrel adapted to receive a portion of the plunger rod therethrough during transition from the collapsed position to the extended position.

12. The syringe assembly of claim 1, further comprising a collar member extending from the handle portion.

13. The syringe assembly of claim 12, further comprising a second plunger rod comprising a second depending leg having a proximal end and a distal end, and a second hinge connecting the second depending leg to the handle portion at the proximal end, wherein the collar member defines a first window adjacent the plunger rod and a second window adjacent the second plunger rod.

14. The syringe assembly of claim 13, wherein the plunger rod and the second plunger rod are oriented on substantially opposite sides of the collar member.

15. The syringe assembly of claim 13, wherein the plunger rod and second plunger rod deflect into the collar member in the extended position.

16. The syringe assembly of claim 12, wherein the collar member is adapted to be disposed over the exterior surface of the syringe barrel and the plunger rod is adapted to be at least partially disposed within the chamber in the extended position.

17. The syringe assembly of claim 1, further comprising a medication or drug disposed within the chamber of the syringe barrel.

18. A syringe assembly, comprising:
a syringe barrel having a first end, a second end, and a sidewall extending therebetween having an exterior surface and an interior surface defining a chamber;
a stopper comprising a stopper adapter having an engagement, the stopper disposed within the chamber of the syringe barrel; and
a plunger assembly comprising:
a handle portion;
a first elongated plunger rod comprising a first depending leg and a first hinge connecting the first depending leg to the handle portion; and
a second elongated plunger rod comprising a second depending leg and a second hinge connecting the second depending leg to the handle portion,
wherein the plunger assembly is adapted to transition from a collapsed position, in which the entirety of the first elongated plunger rod and the entirety of the second elongated plunger rod are located exterior to the syringe barrel and at least a portion of the first depending leg and at least a portion of the second depending leg extend along at least a portion of the exterior surface of the syringe barrel, to an extended position in which at least a portion of the first depending leg and at least a portion of the second depending leg surround the engagement of the stopper.

19. The syringe assembly of claim 18, wherein the first depending leg defines a first recess therein and the second depending leg defines a second recess therein, wherein the engagement is received within the first recess and the second recess in the extended position.

20. A syringe assembly, comprising:
a syringe barrel having a first end, a second end, and a sidewall extending therebetween having an exterior surface and an interior surface defining a chamber;
a stopper disposed within the chamber of the syringe barrel; and
a plunger assembly comprising an elongated plunger rod and a handle portion connected thereto, the plunger rod comprising a depending leg and at least one hinge connecting the depending leg with the handle portion, the depending leg having an inner surface substantially corresponding to the exterior surface of the syringe barrel,
wherein the plunger rod is adapted to transition from a collapsed position, in which the entirety of the plunger rod is external to the syringe barrel and at least a portion of the depending leg extends along at least a portion of the exterior surface of the syringe barrel, to an extended position in which at least a portion of the depending leg engages the stopper.

* * * * *